US011485952B2

(12) United States Patent
Kissling et al.

(10) Patent No.: US 11,485,952 B2
(45) Date of Patent: Nov. 1, 2022

(54) CELL SEPARATION DEVICE AND USE OF A FLOW FORMATION FOR THE CELL SEPARATION DEVICE

(71) Applicants: Hamilton Bonaduz AG, Bonaduz (DE); Fraunhofer-Gesellschaft zur Förderung der angewandten Forschung e. V., Munich (DE)

(72) Inventors: Tom Kissling, Basel (CH); Jens Grosch, Basel (CH); Thomas Zumstein, Basel (CH); Andrea Traube, Stuttgart (DE); Carsten Etzold, Bonaduz (DE); Tobias Seiler, Films Dorf (CH)

(73) Assignees: Hamilton Bonaduz AG, Bonaduz (CH); Fraunhofer-Gesellschaft zur Förderung der angewandten Forschung e. V., Munich (DE)

(*) Notice: Subject to any disclaimer, the term of this patent is extended or adjusted under 35 U.S.C. 154(b) by 436 days.

(21) Appl. No.: 16/077,588

(22) PCT Filed: Feb. 9, 2017

(86) PCT No.: PCT/EP2017/052812
§ 371 (c)(1),
(2) Date: Aug. 13, 2018

(87) PCT Pub. No.: WO2017/137472
PCT Pub. Date: Aug. 17, 2017

(65) Prior Publication Data
US 2019/0032002 A1    Jan. 31, 2019

(30) Foreign Application Priority Data
Feb. 12, 2016    (DE) .................... 10 2016 202 139.7

(51) Int. Cl.
*C12M 1/00*    (2006.01)

(52) U.S. Cl.
CPC .................................. *C12M 47/04* (2013.01)

(58) Field of Classification Search
CPC ................. B01F 2005/0005; B01F 2005/0025
See application file for complete search history.

(56) References Cited

U.S. PATENT DOCUMENTS

| 3,794,300 A * | 2/1974 | Harder | B01F 5/0656 |
| | | | 366/339 |
| 4,840,493 A * | 6/1989 | Horner | B01F 5/0615 |
| | | | 138/42 |

(Continued)

FOREIGN PATENT DOCUMENTS

| DE | 44 35 717 | 1/1996 |
| DE | 20 2012 002 102 | 6/2013 |

(Continued)

OTHER PUBLICATIONS

English language machine translation of DE 202012002102 U1, generated Feb. 3, 2021. (Year: 2021).*

(Continued)

*Primary Examiner* — David C Mellon
(74) *Attorney, Agent, or Firm* — Tollefson IP (57) ABSTRACT

A cell separation apparatus a container for reception of a cell suspension and a conduit connected to the container for the conveyance of cell suspension out of the container. The conduit extends along a notional conduit path passing centrally through the conduit, the conduit path defining in the conduit an axial direction proceeding along the conduit path, a radial direction orthogonal to the conduit path, and a circumferential direction proceeding around the conduit path. A segment of the conduit constitutes a turbulent flow segment including a flow configuration. The flow configu- (Continued)

ration includes at least two axial configuration segments located axially behind one another to accelerate a cell suspension.

19 Claims, 2 Drawing Sheets

(56) References Cited

U.S. PATENT DOCUMENTS

| | | | | |
|---|---|---|---|---|
| 5,069,881 | A | * | 12/1991 | Clarkin ................ B29B 7/7452 422/135 |
| 6,840,281 | B1 | * | 1/2005 | Amidzich ................ B67D 1/14 138/37 |
| 7,041,218 | B1 | * | 5/2006 | Liles .................... B01F 5/0646 209/434 |
| 2005/0106452 | A1 | * | 5/2005 | Qureshi ................ H01M 50/60 366/339 |
| 2009/0233348 | A1 | | 9/2009 | Danner et al. |
| 2012/0258536 | A1 | | 10/2012 | Aidun et al. |
| 2013/0078163 | A1 | | 3/2013 | Chung et al. |
| 2013/0205729 | A1 | * | 8/2013 | Qureshi ................ B01D 45/08 55/456 |
| 2015/0355072 | A1 | | 12/2015 | Hayden et al. |
| 2017/0037381 | A1 | | 2/2017 | Coffman et al. |

FOREIGN PATENT DOCUMENTS

| | | |
|---|---|---|
| DE | 10 2013 200 927 | 7/2014 |
| WO | 2008/019964 | 2/2008 |
| WO | 2011/043731 | 4/2011 |
| WO | 2015/158776 | 10/2015 |

OTHER PUBLICATIONS

International Search Report issued in PCT/EP2017/052812.
German Search Report issued in DE 10 2016 202 139.7.

* cited by examiner

CELL SEPARATION DEVICE AND USE OF A FLOW FORMATION FOR THE CELL SEPARATION DEVICE

CROSS REFERENCE TO RELATED APPLICATIONS

This application is the National Stage of International Application No. PCT/EP2017/052812, filed on Feb. 9, 2017, which claims the benefit of German Application No. 10 2016 202 139.7, filed on Feb. 12, 2016. The contents of both applications are hereby incorporated by reference in their entirety.

DESCRIPTION

The present invention relates to a cell separation apparatus, encompassing a container for reception of a cell suspension and a conduit connected to the container for the conveyance of cell suspension out of the container, the conduit extending along a notional conduit path passing centrally through the conduit, the conduit path defining in the conduit an axial direction proceeding along the conduit path, a radial direction orthogonal to the conduit path, and a circumferential direction proceeding around the conduit path, at least a segment of the conduit, constituting a turbulent flow segment, comprising a flow configuration that generates a turbulent cell suspension flow.

The present invention further relates to use of a flow configuration in order to separate cells in a cell suspension.

A cell separation apparatus of the species is known from WO 2008/067044 A.

A fundamental problem with cell cultures is that the cultured cells present in a cell suspension after being harvested are often not present in completely separated fashion, but exist in part as cell clusters or cell agglomerations in which several cells are joined to one another.

These cell agglomerations are disadvantageous because the cells joined in them cover one another, so that the surface area, wettable by the liquid of the cell suspension, of an agglomerated cell differs in size depending on the number of cells joined to that cell. Because cells take in nutrients through the membrane of their cell wall, the cells of a cell agglomeration have different levels of access to nutrients contained in the suspension liquid. In addition, contact among the cells often limits the cell growth of the cells joined to one another, increasingly so as the number of adjacent cells in mutual contact rises.

Because of the mechanisms discussed, cell clusters or cell agglomerations in cell suspensions thus result in differences in the development of cells in cell culture; as a rule, cell agglomerations disadvantageously influence the cell culture yield. Cell mortality in cell agglomerations furthermore rises compared with the cell mortality of individual cells.

WO 2008/067044A of the species discloses a conduit that conveys a cell suspension and has a turbulent flow segment that is constituted by flow obstacles in the conduit. Two flow obstacles, which have flowthrough-capable hole patterns offset from one another, are arranged at a distance from one another in a flow direction.

As flow occurs through the two hole patterns in the flow obstacles that constitute the flow configuration of the existing art, the result is that a degree of turbulence with which cell agglomerations are dissolved, and the agglomerated cells are separated, is achieved in the flowing cell suspension.

A disadvantage of the known flow configuration of the cell separation apparatus of the species is its small flow-through cross section, since in order to achieve the desired degree of turbulence the known flow obstacles exhibit, in the least obstructive case, only 50% of the flow cross section of the conduit conveying the cell suspension without a flow configuration. The hole pattern of the known flow obstacles can be constricted to the point that the passthrough cross section of the flow obstacles is equal to only 1% of the flow cross section of the flow-conveying conduit without a flow configuration.

The object of the present invention is therefore to describe a technical teaching that, in a context of at least the same separation success and for the same flow-capable conduit cross section without a flow configuration, permits a higher volumetric throughput per unit time, thereby demonstrably increasing the cost-effectiveness of the cell separation apparatus.

This object is achieved according to the present invention in that the flow configuration comprises at least two axial configuration segments located axially behind one another, one of which is embodied to accelerate a cell suspension, flowing through the conduit axially away from the container, in a circumferential direction in a first directional orientation, and the respective other of which is embodied to accelerate the cell suspension in a circumferential direction in a second directional orientation opposite to the first directional orientation.

According to a further inventive concept linked to the aforesaid one by a common inventive idea, this object is also achieved by the use of a flow configuration that extends along a notional configuration path passing centrally through the flow configuration, the configuration path defining an axial direction proceeding along the configuration path, a radial direction orthogonal to the configuration path, and a circumferential direction proceeding around the configuration path, the flow configuration comprising at least two axial configuration segments located axially behind one another, of which the one axial configuration segment is embodied to accelerate a fluid, flowing through the conduit axially away from the container, in a circumferential direction in a first directional orientation, and of which the respective other axial configuration segment is embodied to accelerate the fluid in a circumferential direction in a second directional orientation opposite to the first directional orientation, to separate cells in a cell suspension constituting the flowing fluid.

It is principally the cell separation apparatus that will be explained and refined below; refinements of the flow configuration are also to be understood as refinements of the use of the flow configuration, with the stipulation that in the context of refinement of the use claims, the term "conduit path" is to be replaced by the term "configuration path."

The conduit path and configuration path in fact proceed collinearly in the operationally ready cell separation apparatus. But because the use claim is directed toward the use of a flow configuration on its own, what is used here instead of the conduit-based coordinate system is the coordinate system, referred directly to the flow configuration, of the configuration path.

Explanations of the cell separation apparatus which refer to the conduit wall are to be understood, in terms of the use claim, as explanations that are directed toward the radially outer edge of the flow configuration. When the flow configuration extends radially as far as the conduit wall, the "radially outermost edge" radial coordinate of the flow configuration refers to the same radial location as the "conduit wall" radial coordinate.

Directions in addition to the axial direction which are mentioned in some circumstances in the description of the cell separation apparatus, for example "toward that longitudinal end of the conduit which is closer to the container" or "away from the container," are intended to be immaterial with regard to the use of the flow configuration. All that is important here is the axial direction defined by the configuration path, regardless of the two concretely possible axial directional orientations.

The reason for this allocation of terms between the terms used to describe the cell separation apparatus according to the present invention, and the understanding to be taken as a basis for those terms with regard to refinement of the use of the flow configuration, is that the flow configuration does not need to be embodied integrally with the respective conduit but can also exist as a separate configuration component independently of the conduit, so that in the latter case the conduit-based coordinate system, which is advantageous for describing the cell separation apparatus, is not applicable.

The basic idea of the present invention is that of accelerating the axial flow in the conduit, additionally to the axial motion, to perform oppositely directed circumferential motions as a result of the axial configuration segments located axially behind one another. An aperture plate, as used in the existing art of the species, can thereby be omitted. A sufficient degree of turbulence can thus be achieved without the cross-sectional constrictions of the flow cross section which are typical of the aperture plate of the existing art.

The cell separation apparatus of the existing art achieves the degree of turbulence in an axially very short space using two axially successive aperture plates, but the placement space available between the container and the conduit end, remote from the container, of the conduit as a rule is not critical, especially since the conduit does not need to proceed in extended fashion, i.e. with a rectilinear conduit path, but can instead be wound into a coil, spiral, and the like. The cell separation apparatus according to the present invention therefore requires a longer axial conduit segment than the apparatus of the existing art of the species in order to achieve a high degree of turbulence, but this can be achieved with a cross-sectional reduction in the flow cross section of the conduit which, compared with the identical conduit without a flow configuration, does not exceed 15%, preferably 10%, of the identical flow cross section without a flow configuration. A substantially larger quantity of cell suspension per unit time can therefore be made turbulent, and the cells contained therein can thus be reliably separated. The slightly longer axial conformation of the conduit is therefore more than compensated for by the considerably elevated volumetric throughput per unit time.

The intention here is that axially successive axial configuration segments be embodied to accelerate the cell suspension, flowing in principle axially through the conduit, in opposite circumferential directions. The result is to achieve, in the cell suspension, turbulence which is sufficient for separation of the cell agglomerates possibly contained therein. This is furthermore achieved in particularly gentle fashion, which has an advantageous effect on cell viability. Many cells have little capacity for mechanical loads, especially as caused by shear loads that often occur in flows (shear stress). As a result of the axially alternating acceleration, occurring here, of the suspension flow in opposite circumferential directions, a high degree of turbulence is achieved without undesirably high shear loads. The separation result, determined e.g. by the number of cell agglomerates contained in a predetermined quantity of cell suspension after passage through the flow configuration as compared with the number thereof before passing through the flow configuration, is outstanding.

The consequence of the oppositely directed circumferential accelerations can be that as the cell suspension flows through the turbulent flow segment it flows, always in the same directional orientation but at different speeds, in a circumferential direction. In the interest of an advantageously higher degree of turbulence, however, it is preferred if the at least two axial configuration segments located axially behind one another are embodied to impart to the cell suspension flowing axially through them, in an upstream axial configuration segment, a flow component proceeding in a circumferential direction in a first directional orientation, and to impart to the cell suspension, in a downstream axial configuration segment, a flow component proceeding in a second directional orientation opposite to the first directional orientation. In this case the flow component of the cell suspension in a circumferential direction changes not only in terms of quantity but also in terms of its directional orientation.

In order to achieve a particularly high degree of turbulence in the cell suspension, the preferred application instance that of the at least two axial configuration segments, the one axial configuration segment is embodied to impart to the flow of fluid axially impinging on the axial configuration segment a flow component in a circumferential direction proceeding in a first directional orientation, and that the respective other axial configuration segment is embodied to impart to the fluid a flow component proceeding in a circumferential direction in a second directional orientation opposite from the first direction component, also applies to the use.

It is sufficient in this context if the flow of fluid or cell suspension also impinges axially on the axial configuration segments, i.e. has, in addition to the axial flow component, flow components in other flow directions (radially and/or in a circumferential direction). The flow in the conduit or through the flow configuration does not need to be exclusively axial at any point.

The separation result can be improved, while cell viability remains high, by the fact that the axial length of the flow configuration, and the number of directional orientation changes in the acceleration of the flow in a circumferential direction which take place over that axial length, are increased. According to an advantageous refinement of the cell separation apparatus, provision is therefore made that the flow configuration comprises a plurality of axial configuration segments located axially behind one another, of which each axial configuration segment axially succeeding another axial configuration segment is embodied to accelerate the cell suspension, flowing through the conduit in an axial direction away from the container, in a circumferential direction in a directional orientation which is directed oppositely from the directional orientation of the acceleration in a circumferential direction in the axially immediately preceding axial configuration segment.

An "axial configuration segment" for purposes of this Application is always intended to be an axial segment of the flow configuration in which the suspension flow is accelerated in a circumferential direction in a uniform directional orientation. When the directional orientation of the flow acceleration in a circumferential direction changes, a new axial configuration segment begins, and it extends axially until the directional orientation of the acceleration of the suspension flow in a circumferential direction reverses again.

In the interest of attaining a maximum degree of turbulence, it is furthermore preferred if what changes as a result of the circumferential accelerations in opposite directional orientations is not only the magnitude of the flow speed component of the flowing cell suspension in a circumferential direction, but the directional orientation of the motion itself. It is consequently preferred if, of the plurality of axial configuration segments located axially behind one another, each axial configuration segment axially succeeding another axial configuration segment is embodied to impart to the cell suspension flowing through the conduit in an axial direction away from the container a flow component, proceeding in a circumferential direction, whose circumferential directional orientation is directed oppositely to that in the axially immediately preceding axial configuration segment.

The flow configuration preferably encompasses at least eight axial configuration segments.

Those skilled in the art usually know how an axial flow in a conduit can be equipped with a flow component in a circumferential direction, i.e. can be accelerated or deflected in a circumferential direction. Any type of flow influence that, in axially successive axial configuration segments, accelerates the cell suspension in a circumferential direction in opposite directional orientations is suitable for achieving the result according to the present invention.

According to an advantageous refinement of the present invention, the flow configuration can therefore physically comprise, in at least two axial configuration segments, at least one respective directing surface that is inclined with respect to the conduit path in such a way that the normal vector of the directing surface, by definition pointing away from the directing surface, on the one hand has an axial component that points in an axial direction toward that longitudinal end of the conduit which is closer to the container and from which the cell suspension flows, and has a circumferential component that points in a circumferential direction. In order to accelerate the cell suspension in a circumferential direction in opposite directional orientations in axial configuration segments located axially behind one another, the circumferential components of the normal vectors of directing surfaces of axial configuration segments located axially behind one another point in opposite directions. The flow configuration comprises at least one such directing surface preferably in more than two axial configuration segments, particularly preferably in each of its axial configuration segments.

In a particularly simple case the directing surface can be a flat surface that can be set with reference to the conduit path at a setting angle around a setting axis that proceeds in a radial direction. The setting axis can, but does not need to, intersect the conduit path, but can also proceed at a distance from it.

In addition, especially in the case discussed above of a flat surface constituting a directing surface, the directing surface can be rotated around a rotation axis parallel to the conduit path, in particular in such a way that the normal vector of the directing surface also has a component radially inward toward the conduit path.

At least at the axial inflow end of an axial configuration segment, the setting angle of the directing surface is no greater than 45° with respect to a plane at the same point containing the conduit path, so that the dynamic pressure at the inflow end of an axial configuration segment is not unnecessarily raised.

The setting angle of a directing surface in an axial configuration segment can become larger with increasing axial distance from the axial inflow end, so that with increasing axial distance from the inflow end, the flow component in a circumferential direction in the relevant axial configuration segment becomes increasingly greater. The directing surface can then be constituted from a plurality of flat surface segments, each two of which that directly succeed one another in a circumferential direction are angled with respect to one another. The setting angle can, however, also be constant over the axial length of an axial configuration segment, or can also be constant over the axial length of the entire flow configuration over all the directing surfaces.

In principle, the directing surface of an axial configuration segment can extend radially inward beyond the conduit path, proceeding from a conduit wall that radially externally delimits the flow region of the conduit. For particularly effective deflection of the suspension flow in a circumferential direction, however, it is advantageous if at least one axial configuration segment of the flow configuration comprises at least two directing surfaces. The two directing surfaces are then respectively arranged in the same axial region of the conduit, respectively in a radial region between the conduit path and conduit wall but in different circumferential regions. Preferably a plurality of axial configuration segments, particularly preferably each axial configuration segment of the flow configuration, is embodied in such a way.

In order to produce a maximally homogeneous flow in an axial configuration segment, the two or more directing surfaces of an axial configuration segment are preferably embodied symmetrically with respect to the conduit path in such a way that the one directing surface is transformable, by rotation around the conduit path, into a respective other directing surface of the same axial configuration segment.

It is the case in this context that the greater the number of directing surfaces that are provided in different circumferential segments in an axial configuration segment, on the one hand the more reliable the acceleration of the cell suspension in a circumferential direction, but on the other hand also the greater the decrease in the flowthrough-capable conduit cross section, since the directing surfaces, constituting physical objects, occupy volume in the conduit segment in which they are arranged. It is preferred here if for each axial configuration segment exactly two or three directing surfaces are arranged, offset with respect to one another in a circumferential direction, preferably offset equidistantly by 180° (two directing surfaces) or 120° (three directing surfaces).

For maximally smooth acceleration (therefore with little shear load) of the cell suspension flow in a circumferential direction, the at least one directing surface of an axial configuration segment can be embodied helically. Preferably all the directing surfaces of an axial configuration segment, particularly preferably of all axial configuration segments, are embodied helically.

The pitch angle of the helical directing surface is defined by a plane tangent to the directing surface, which is curved as a result of its helical configuration. The pitch angle can in turn increase toward the axial outflow end with increasing axial distance from the axial inflow end of the axial configuration segment. Preferably, however, the pitch angle is constant over the entire axial length of the directing surface. When an axial configuration segment comprises more than one directing surface, preferably the pitch angles of the all the directing surfaces at the same axial position are identical.

Preferably the pitch angles of a directing surface, in particular of all directing surfaces, are constant over the entire axial length of an axial configuration segment. Preferably the pitch angles of all directing surfaces of all axial configuration segments are of constant magnitude and identical in size, and differ between the different axial configuration segments only in terms of their differing sign, in order to be able to provide, due to their differing pitch, the acceleration of the suspension flow in a circumferential direction in opposite directional orientations.

In principle, the helical directing surface of an axial configuration segment can encircle the notionally central conduit path or configuration path any number of times. For a particularly effective and therefore economical flow configuration, however, it is sufficient and advantageous if the helical directing surface extends along its axial dimension exactly sufficiently far in a circumferential direction around the conduit path that the suspension flowing along it has an unequivocal acceleration, or even motion, imparted to it before the flow flows into the axially successive axial configuration segment and is accelerated, or even moved, therein in a circumferential direction in the opposite directional orientation. The acceleration of a portion of the total cell suspension flow approximately 60% of the mass flow or more, in a circumferential direction is sufficient in this context. Experiments have shown that it is sufficient in this context if the helical directing surface sweeps out along its axial extent at least, preferably exactly, an angle of 180° around the conduit path. This applies preferably to all directing surfaces of a given axial configuration segment. A particularly low-loss flow axially through the conduit and along the flow configuration can be achieved, in the context of an axial sequence of axial configuration segments acting acceleratingly in a circumferential direction in opposite directional orientations, by the fact that the axially inflow-side edge of a directing surface of one axial configuration segment is arranged with an offset, preferably arranged with a 90° or 180° offset, in a circumferential direction with respect to the axially outflow-side edge of a directing surface of the immediately preceding (upstream) axial configuration segment. It is of course also conceivable for the directing surfaces of different axially successive axial configuration segments to proceed with an edge-free transition into one another, although a lower degree of turbulence then is achieved for the same axial length of the flow arrangement; this can be advantageous for particularly sensitive cells. The continuous edge-free embodiment of a single directing structure, having different directing-surface segments that are associated with the respective axial configuration segments, is nevertheless not to be precluded by the present Application.

It is furthermore conceivable in principle to embody the flow configuration in one piece with the conduit, for example by the fact that the conduit is constituted from comparatively flexible silicone plastic. Silicone plastic of this kind permits, after curing, nondestructive unmolding of a mold core, constituting the flow configuration radially internally in the conduit, in an axial direction in which the cell suspension ultimately also flows through the conduit during operation. For example, in the context of an embodiment of the flow configuration in one piece with the conduit, the directing surfaces of the axial configuration segments can project radially inward from the conduit wall; they do not necessarily need to proceed radially inward as far as the center of the conduit, i.e. to the location of the virtual conduit path.

Preferably, however, the flow configuration is embodied on a configuration component embodied separately from the conduit. This on the one hand has an advantage in terms of production engineering, since a configuration component of this kind, constituting a separate component, can be manufactured substantially more simply and inexpensively, and with greater design freedom, than a flow configuration extending in one piece radially inside the conduit.

A suitable configuration component, constituting a mixer component for effective blending of two components of a mixed product, is known from DE 20 2012 002 102 U1. Whereas in the aforesaid document the configuration component is used to mix different liquid components, according to the present invention it is used to separate cell agglomerations in a liquid.

A further advantage of separate embodiment of the configuration component is the considerably improved capability for cleaning and optionally sterilizing the conduit and flow configuration after use, so that the conduit and flow component can be used again for a different cell suspension with no risk of contamination of the cell suspension by the conduit and flow configuration as a result of previous use.

In order to allow cell suspension to flow through the conduit in the context of a predefined axial flow speed component, with a long turbulence duration and thus in turn with good separation results along with high cell viability, the configuration component is preferably deformable so that it is introducible even into a physically long conduit that does not proceed rectilinearly. The conduit is preferably helically coiled in order to achieve the longest possible axial turbulence length, so that it is particularly advantageous for the configuration component if it is flexible, in particular around one or several flexure axes that enclose an angle with the conduit path. The angle between the flexure axes and the conduit path is preferably a right angle.

The conduit is preferably also deformable, so that depending on the application it can be brought, respectively within the context of its deformability, into a suitable shape.

The configuration component is preferably manufactured as an injection-molded component, the deformability then advantageously being adjustable by way of the material thickness of the directing structure comprising the directing surfaces.

In order to stabilize the flow configuration, in particular the configuration component, it can comprise a support structure extending at least along an axial segment of the flow configuration, preferably axially along the entire flow configuration, with which the directing surfaces are connected, preferably connected in one piece, at their radially inner end. The supporting structure is preferably a central rod structure or column structure, consequently a core of the configuration component, whose radial dimension is preferably smaller than the radial dimension of the flow configuration in order to avoid unnecessary flow obstacles.

Cell separation using the apparatus according to the present invention can advantageously be accomplished in a completely closed system, with no contact occurring between the cell suspension and the atmosphere. A collection container, into which the cell suspension having the separated cells is delivered, can be arranged at the downstream end of the conduit.

The present invention will be explained in more detail below with reference to the appended drawings, in which.

Figure 1:
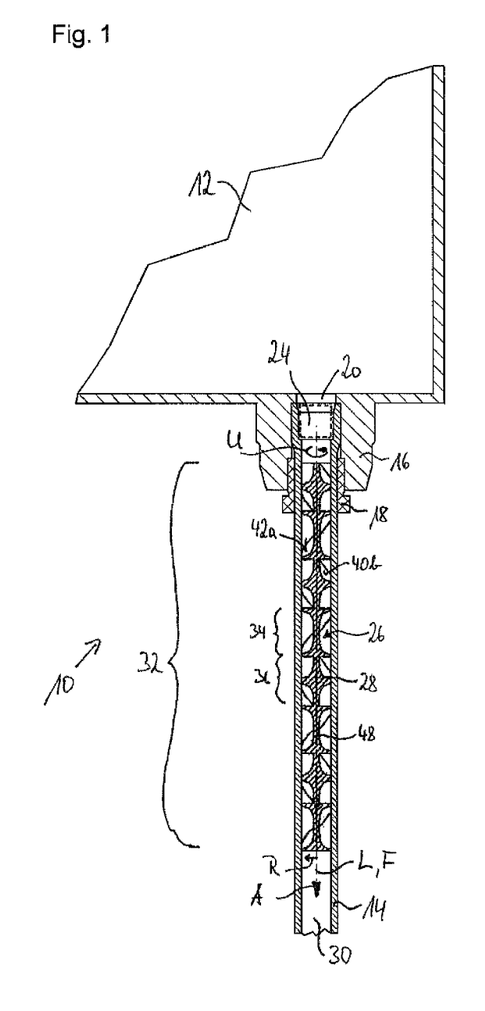
FIG. 1 schematically depicts, by way of an embodiment according to the present invention, a cell separation apparatus of the present Application in longitudinal section.

In FIG. 1, an embodiment according to the present invention of a cell separation apparatus of the present Application is labeled in general with the number 10. It encompasses a container 12, for example a cell culture container, only a corner region of which is depicted in the schematic longitudinal section of FIG. 1.

Container 12 is adjoined by a conduit 14, for example a flexible hose conduit 14.

Hose conduit 14 is coupled to an outlet configuration 16 of cell culture container 12 and retained in position there, in particular against being pulled out of outlet configuration 16, by means of a threaded retainer 18.

Outlet configuration 16 is depicted merely schematically in FIG. 1. In the example depicted, conduit 14 is permanently coupled to outlet configuration 16. This need not be the case. Conduit 14 can also be insertable, and thus quickly connectable and releasably couplable to outlet configuration 16, via attachment or coupling configurations known per se. An insertable connection of this kind can at least be established and undone more quickly than is the case using threaded retainer 18. The nature of the flow connection between conduit 14 and an outlet opening 20, surrounded by outlet configuration 16, of cell culture container 12 is, however, not relevant in the present case.

A valve arrangement 24 acting in known fashion, by way of which a flow connection between conduit 14 and outlet opening 20 can be selectably established or blocked, can be arranged in region 24 in attachment configuration 16 outlined with dashed lines, and also in conduit 14. Valve arrangement 24 can be switchable, in a manner known per se, in contactless fashion by magnetic field manipulation from outside outlet configuration 16, for example by modifying a magnetic field acting on valve arrangement 24 from outside outlet configuration 16, with the result that a ferromagnetic valve body can be displaceable between a flowthrough position and a blocking position.

In the present example, cell culture container 12 serves for the culturing of adherent cells that initially grow adheringly on a culture surface in cell culture container 12 and detach from their culture surfaces after addition of a corresponding dissolution agent to the liquid present in cell container 12, so that the cells can then float freely in the liquid in cell culture container 12 and thus form, together with the liquid in cell culture container 12, a cell suspension. The cells dissolved in the cell suspension are ready to harvest and are usually removed from cell culture container 12, in the present example through outlet opening 20, shortly after detachment from their culture surfaces.

It usually happens that the cells are not received in completely separated fashion in the liquid in cell culture container 12, but instead that cell agglomerations made up of a varying number of mutually adhering cells form therein. Separated cells are desirable, however, since, as indicated in the introduction to the description of this Application, the cell agglomerations have a predominantly disadvantageous effect on the development and further processability of the cultured cells.

A flow configuration 26, constituted in the example depicted by a configuration component 28 embodied separately from conduit 14 and arranged therein, is provided in conduit 14 in order to separate the cells out of the undesired cell agglomerations. Configuration component 28 is also depicted in isolation, in perspective, in FIG. 2.

The physical proximity of flow configuration 26 to outlet opening 20 in FIG. 1 is preferred. Flow configuration 26 can in fact be arranged at any desired point in conduit 14. Additional conduits (not depicted in FIG. 1) can furthermore be interposed between conduit 14 and outlet configuration 16.

Conduit 14, which is likewise depicted for the sake of simplicity as a rectilinear conduit 14, extends along a notional conduit path L passing through centrally along a flowthrough-capable conduit cavity 30. Because flow configuration 26 is arranged in conduit 14 collinearly therewith, conduit path L is at the same time also configuration path F, along which flow configuration 26 and configuration component 28 extend (see also FIG. 2).

Flow configuration 26, like conduit 14, is flexible and can be curved around any flexure axes. It can in particular be rolled up in space-saving fashion into a coil and the like.

Flow configuration 26 serves in the present case, along its extent, as a turbulent flow segment 32 of conduit 14 in order to provide, at least in that turbulent flow segment 32, a turbulence that separates the cell agglomerations in the cell suspension flowing through it.

Figure 2:
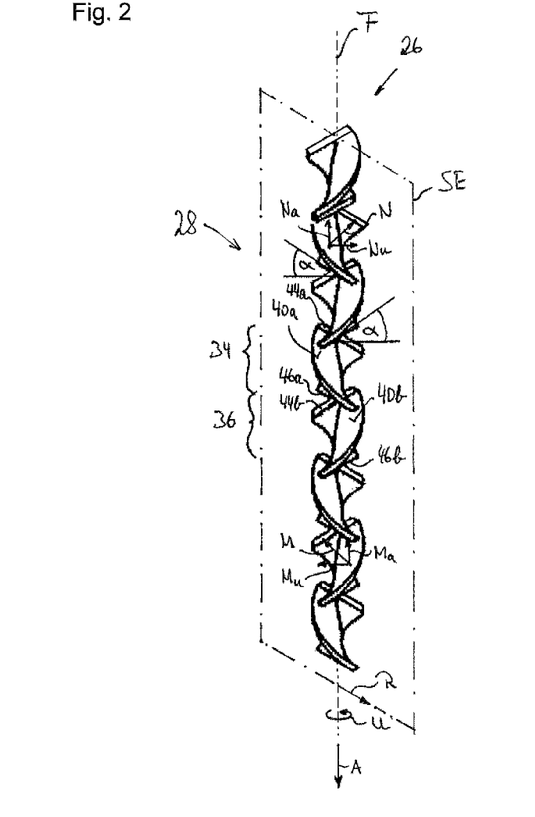
FIG. 2 is a perspective view of the configuration component used in the cell separation apparatus of FIG. 1.

Flow configuration 26 comprises for that purpose several axial configuration segments arranged axially behind one another, of which only axial configuration segments 34 and 36, which are arranged in flow configuration 26 alternatingly in an axial direction, will be explained in further detail below.

Conduit path L and configuration path F define an axial direction A. They furthermore define a radial direction R orthogonal to the axial direction, and a circumferential direction U surrounding the respective paths L and F.

The natural directional orientation of axial direction A is directed away from cell culture container 12. The natural directional orientation of radial direction R is directed away from the respective path L or F, and the natural directional orientation of the circumferential direction is counter-clockwise when viewed in the natural axial direction.

Axial configuration segments 34 and 36 that alternate successively in axial direction A serve to accelerate a cell suspension, which flows axially through turbulent flow segment 32, in circumferential direction U alternatingly in opposite directional orientations.

Section plane SE, along which flow configuration 26 or configuration component 28 is shown sectioned in FIG. 1, is depicted with dot-dash lines in FIG. 2. Section plane SE contains configuration path F.

Axial configuration segments 34 are embodied to accelerate a cell suspension, which flows in the natural axial direction A through conduit 14 or flow configuration 26, in circumferential direction U in the natural directional orientation, i.e. counter-clockwise when viewed in the natural axial direction.

Axial configuration segments 36, on the other hand, are embodied to accelerate the cell suspension flowing through them in the circumferential direction in the opposite directional orientation, i.e. clockwise when viewed in the natural directional orientation of axial direction A. Both axial configuration segments 34 and axial configuration segments 36 have respective directing surfaces 40a and 40b for this purpose. Directing surfaces 40a and 40b, which respectively extend radially outward from configuration path F, proceed in helical fashion with mutually opposite twists. In fact, both axial configuration segments 34 and axial configuration segments 36 respectively comprise a second directing surface in addition to directing surface 40a and 40b, but it always faces away from the viewer in FIG. 2. The two directing surfaces of each axial configuration segment 34 or 36 are constructed symmetrically with respect to one another in such a way that they are transformable into one another by rotation around configuration path F, in each case by a 180° rotation in the example depicted.

The description of directing surfaces 40a and 40b thus also applies to the respective second directing surface of the same respective axial configuration segment 34 and 36. A portion of second directing surface 42a of axial configuration segments 34 is visible only in FIG. 1.

The helical directing surfaces 40a, 42a, and 40b, as well as the further directing surface (not visible) of axial configuration segment 36, have over their axial extent a constant pitch angle α that is of the same magnitude for both axial configuration segments 34 and 36, and is merely directed oppositely.

The helical directing surface 40a thus has a normal vector N that has an axial component Na that points axially in the direction from which flow impinges on the directing surface, and has a component Nu that points in a circumferential direction in the directional orientation in which the flow striking directing surface 40a is accelerated.

Directing surfaces 40b also have normal vectors M whose axial component Ma is identical in terms of magnitude and direction with respect to the axial component Na of normal vector N of directing surface 40a. Circumferential directional component Mu of normal vector M of directing surface 40b is furthermore identical in magnitude, but oppositely directed, with respect to circumferential directional component Nu of normal vector N of directing surface 40a. Acceleration of the cell suspension flowing through axial configuration segments 34 and 36 in circumferential direction U in opposite directional orientations is thereby obtained.

The directing surfaces of a given axial configuration segment respectively extend 180° in a circumferential direction, and thus constitute half a basic screw thread.

Because the two directing surfaces of a given axial configuration segment are arranged with a 180° offset from one another in a circumferential direction, they form, orthogonally to configuration path F, both a rectilinear axially inflow-side edge 44a for axial configuration segments 34 and 44b for axial configuration segments 36, and, orthogonally to configuration path F, a rectilinear axially outflow-side edge 46a for axial configuration segments 34 and 46b for axial configuration segments 36.

Because directing surfaces 40a, 40b, and 42a of the respective axial configuration segments 34 and 36 twist in their axial dimension 180° in a circumferential direction around configuration path F or conduit path L, the respective axially inflow-side and axially outflow-side edges 44a, 46a and 44b, 46b of a given axial configuration segment 34 and 36 are parallel to one another.

In order to achieve maximally effective turbulence in the cell suspension flowing through conduit 14 having flow configuration 26, and thus maximally thorough separation of the cells present in the cell suspension, the axially inflow-side edges 44a and 44b of a first axial configuration segment 34 or 36 are preferably rotated 90° in terms of the respective axially outflow-side edges 46b and 46a of a second axial configuration segment 36 or 34 immediately axially preceding the first axial configuration 34 or 36.

This crosswise arrangement of the axially successive axial configuration segments 34 and 36 is possible, with no loss of stability in configuration component 28, because configuration component 28 is stabilized by a central support structure or core 48 that, in the present example, extends over the entire axial length of flow configuration 26 or of configuration component 28.

A pump is not depicted in FIG. 1, even though a conveying pump for generating a flow of cell suspension flowing axially through conduit 14 away from cell culture container 12 can be present. A pump is not obligatorily necessary, however. Additionally or alternatively, a flow of cell suspension through conduit 14 past flow configuration 26 can be gravity-induced. Also additionally or alternatively, the flow can be generated by generating an excess pressure in a gas bladder in cell culture container 12, so that the excess gas pressure in cell culture container 12 expels the cell suspension out of container 12 via outlet opening 20 through conduit 14.

Outstanding separation results are obtained, along with high cell viability, with flow configuration 26 described in the present Application and with the use thereof for cell separation. Depending on how "stubborn" the cell agglomerations present in the cell suspension are, turbulent flow segment 32 can be axially prolonged by arranging several flow configurations 26 or several configuration components 28 behind one another in a conduit 14, thereby extending the turbulence path length traveled by the cell suspension. By adapting the axial length of turbulent flow segment 32, and thanks to the ability of conduit 14 to be coiled up together with flow configuration 26 received therein, cell agglomerations can thus be almost completely removed from any cell suspension without requiring much installation space.

Configuration component 28 can be retained axially in position in conduit 14 in positively engaging fashion, for example by an interaction of projections and recesses, and/or intermaterially, for example using adhesive. Usually, however, a frictional engagement between the inner wall of conduit 14 and the outer edge of configuration component 28 is already sufficient to prevent an axial displacement of configuration component 28 relative to conduit 14 as flow occurs through conduit 14. The frictional engagement becomes that much more sufficient as conduit 14 is arranged with a greater curvature, for example in the above-described helical shape for space-saving arrangement even of longer conduit segments.

If doubts should exist regarding comprehension of the present Application, the conduit carrying the cell suspension is always to be conceived of as a rectilinear conduit along a rectilinear conduit path, even though in reality that is technically not obligatorily necessary.

The invention claimed is:

1. A cell separation apparatus, comprising:
a cell culture container containing a cell suspension, said cell culture container having a culture volume and a single outlet connected to said culture volume;
a conduit having an intake end and a discharge end, said conduit connected fluidly at the intake end only to the single outlet of said cell culture container, for the conveyance of said cell suspension out of the container into the conduit intake end, the conduit extending along a notional conduit path passing centrally through the conduit, the conduit path defining in the conduit an axial direction proceeding along the conduit path, a radial direction orthogonal to the conduit path, and a circumferential direction proceeding around the conduit path; and
a turbulence creating device fixedly positioned within at least one segment of the conduit below said single outlet of said container, constituting a turbulent flow segment, comprising a flow configuration that generates a turbulent cell suspension flow, said flow configuration comprises at least two axial configuration segments located axially behind one another, a first axial configuration segment of said at least two axial configuration segments being embodied to accelerate said cell suspension, flowing through the conduit axially away from the container, in a circumferential direction in a first directional orientation, and a second axial configuration segment of said at least two axial configuration segments being embodied to accelerate the cell suspension in a circumferential direction in a second directional orientation opposite to the first directional orientation.

2. The cell separation apparatus according to claim 1, wherein the second axial configuration segment of said at least two axial configuration segments axially succeeding-said first axial configuration segment of said at least two axial configuration segments and is embodied to accelerate the cell suspension, flowing through the conduit in an axial direction away from the container, in a circumferential direction in a circumferential directional orientation which is directed oppositely from that in the first axial configuration segment.

3. The cell separation apparatus according to claim 1, wherein said at least two axial configuration segments comprises at least one respective directing surface that is inclined with respect to the conduit path in such a way that the normal vector of the directing surface has an axial component that points in an axial direction toward that longitudinal end of the conduit which is closer to the container, and has a circumferential component that points in a circumferential direction opposite to the circumferential component of directing surfaces of axial configuration segments of said at least two axial configuration segments that are located axially behind one another.

4. The cell separation apparatus according to claim 3, wherein at least one axial configuration segment of said at least two axial configuration segments, respectively comprises at least two directing surfaces that are arranged in the same axial region of the conduit in a radial region between the conduit path and conduit wall but in different circumferential regions, the directing surfaces of said at least two axial configuration segments being embodied symmetrically with respect to the conduit path in such a way that the one directing surface is transformable, by rotation around the conduit path, into a respective other directing surface of said at least one axial configuration segment.

5. The cell separation apparatus according to claim 3, wherein the at least one directing surface is embodied helically.

6. The cell separation apparatus according to claim 5, wherein the helical directing surface sweeps out along its an axial extent at least an angle of 180° around the conduit path.

7. The cell separation apparatus according to claim 3, wherein an axially inflow-side edge of a directing surface of one of said at least two axial configuration segments located axially behind another axial configuration segment of said at least two axial configuration segments is arranged with an offset in a circumferential direction with respect to an axially outflow-side edge of a directing surface of said another axial configuration segment of said at least two axial configuration segments.

8. The cell separation apparatus according to claim 1, wherein the flow configuration is embodied on a configuration component separate from the conduit.

9. The cell separation apparatus according to claim 8, wherein the configuration component is deformable.

10. The cell separation apparatus according to claim 1, wherein each axial configuration segment of said at least two axial configuration segments comprises at least one respective directing surface that is inclined with respect to the conduit path in such a way that the normal vector of the directing surface has an axial component that points in an axial direction toward that longitudinal end of the conduit which is closer to the container, and has a circumferential component that points in a circumferential direction, the circumferential components of directing surfaces of axial configuration segments located axially behind one another pointing in opposite directions.

11. The cell separation apparatus according to claim 3, wherein each of said at least two axial configuration segments respectively comprises at least two directing surfaces that are arranged in the same axial region of the conduit in a radial region between the conduit path and conduit wall but in different circumferential regions, the directing surfaces of each axial configuration segment being embodied symmetrically with respect to the conduit path in such a way that the one directing surface is transformable, by rotation around the conduit path, into a respective other directing surface of said respective axial configuration segment.

12. The cell separation apparatus according to claim 3, wherein said flow configuration comprises more than two axial configuration segments and each respective axial configuration segment of said more than two axial configuration segments respectively comprises at least two directing surfaces that are arranged in the same axial region of the conduit in a radial region between the conduit path and conduit wall but in different circumferential regions, the directing surfaces of each axial configuration segment being embodied symmetrically with respect to the conduit path in such a way that the one directing surface is transformable, by rotation around the conduit path, into a respective other directing surface of said respective axial configuration segment.

13. The cell separation apparatus according to claim 3, wherein at least one axial configuration segment of said at least two axial configuration segments, comprises at least two directing surfaces that are arranged in the same axial region of the conduit in a radial region between the conduit path and conduit wall but in different circumferential regions, the directing surfaces of an axial configuration segment being embodied symmetrically with respect to the conduit path in such a way that the one directing surface is transformable, by rotation around the conduit path, into a respective other directing surface of the same axial configuration segment.

14. The cell separation apparatus according to claim 3, wherein an axially inflow-side edge of a directing surface of one of said at least two axial configuration segments located axially behind another axial configuration segment of said at least two axial configuration segments is arranged with a 90° or 180° offset, in a circumferential direction with respect to an axially outflow-side edge of a directing surface of said another axial configuration segment of said at least two axial configuration segments.

15. The cell separation apparatus according to claim 8, wherein the configuration component is flexible around one or several flexure axes that enclose an angle with the conduit path.

16. The cell separation apparatus according to claim 8, wherein the configuration component is flexible.

17. The cell separation apparatus according to claim 8, wherein the configuration component is deformable around one or several flexure axes that enclose an angle with the conduit path.

18. The cell separation apparatus according to claim 15, wherein the angle that the one or several flexure axes enclose with the conduit path is a right angle.

19. The cell separation apparatus according to claim 17, wherein the angle that the one or several flexure axes enclose with the conduit path is a right angle.

\* \* \* \* \*